March 11, 1958 F. MEILLAND Plant Pat. 1,689
ROSE PLANT
Filed Aug. 5, 1957
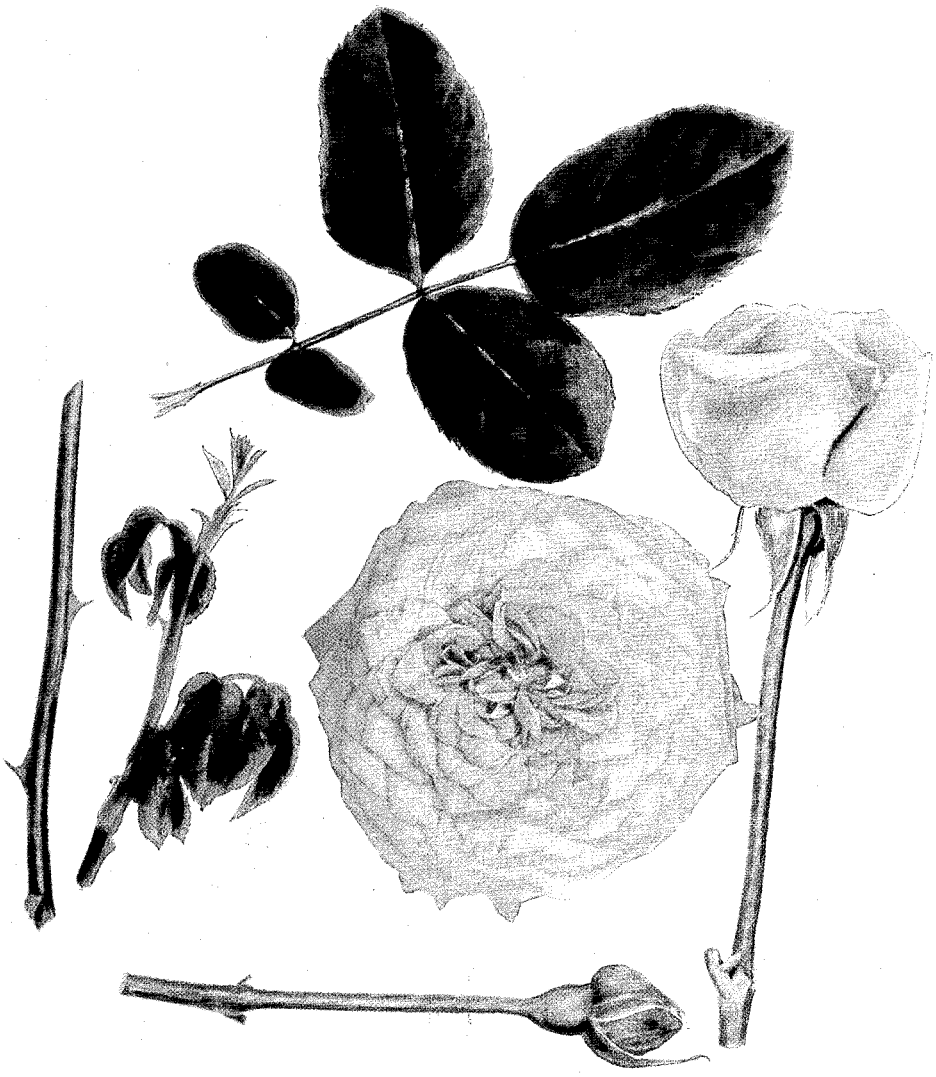
Inventor.
Francis Meilland
By: Robb & Robb
Attorneys.

United States Patent Office

Plant Pat. 1,689
Patented Mar. 11, 1958

1,689

ROSE PLANT

Francis Meilland, Cap Azura, Cap d'Antibes, France, assignor to The Conard-Pyle Company, West Grove, Pa., a corporation of Pennsylvania Application August 5, 1957, Serial No. 676,456

1 Claim. (Cl. 47—61)

The present invention relates to a new and distinct variety of rose plant of the hybrid tea class, which was originated by me by crossing the variety "Happiness," known in France as "Rouge Meilland" (U. S. Plant Patent No. 911) with the variety "Independence," known in Germany as "Kordes' Sondermeldung" (U. S. Plant Patent No. 1,036).

The primary objective of this breeding was to produce a new and improved red rose which combines the most desirable characteristics of the parent varieties. This objective was fully achieved, along with other improvements, as evidenced by the following combination of characteristics which are outstanding and unique in the new variety, and which distinguishes same from its parents, as well as from all other varieties of which I am aware:

(1) A vigorous, bushy, much-branched and upright habit of growth;

(2) Abundant and attractive foliage having good resistance to both mildew and blackspot;

(3) Flowering stems of cutting length which are satisfactory for cut flowers when grown outdoors;

(4) Full and well-formed flowers of exceptionally double form, with the flower petals numbering more than 100 per flower; and (5) An intense, velvety Cardinal Red general color tonality of the flowers and their ability to hold the color throughout their life.

In particular, the plant growth of the new variety is more compact and freer-branching than that of either parent, and the flowers are much heavier-petaled and darker in color than those of either parent.

Asexual reproduction of the new variety by budding, as performed by me in France, and as performed on my behalf at West Grove, Pennsylvania, U. S. A., shows that the foregoing characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; outdoor; seedling; for garden decoration.
Class: Hybrid tea.
Breeding: Seedling.
*Seed parent.*—"Happiness."
*Pollen parent.*—"Independence."
Propagation: Holds its distinguishing characteristics through succeeding propagations by budding.

*Flower*

Locality where grown and observed: West Grove, Pennsylvania, U. S. A.
Flowers borne: Singly to stem; on stems of medium length and normal strength.
Quantity of bloom: Free, outdoors.
Continuity: Continuous.
Fragrance: Slight.
Bud:
*Peduncle.*—Medium length; medium caliper; stiff; almost smooth; with very few green hairs. Color—Fern Green, Plate 0862.
*Before calyx breaks.*—Size—medium. Form—short; ovoid; with a conspicuous neck; with foliaceous appendages on the surface of the bud; with entire foliaceous parts extending beyond the tip of the bud equal to ¼ or more of its length.
*As calyx breaks.*—Color—black, edged with Ruby Red, Plate 827.
*As first petal opens.*—Size—medium. Form—ovoid. Color: outside—Cardinal Red, Plate 822, blotched with black where first exposed to light; inside—Cardinal Red, Plate 822.
*Opening.*—Opens up well.
Bloom:
*Size (when fully open).*—Medium-large; from 3½ to 4½ inches.
*Petalage.*—Very double (many petals, usually with no stamens showing); from 100 to 125 petals; arranged regularly.
*Form.*—Cupped at first, but becoming flat; petals being at first loosely rolled outward, but becoming tightly rolled outward later at maturity.
Petals:
*Texture.*—Thick.
*Appearance.*—Inside—velvety. Outside—shiny.
*Shape.*—Outer petals—obovate, with one or two notches. Intermediate petals—obovate, with one notch. Inner petals—undulate; irregular.

This description of a newly opened flower was made from a rose grown outdoors in the month of September at West Grove, Pennsylvania, U. S. A.:

*Color.*—Outer petal: outside surface—Indian Lake, Plate 826, with base of petal Magenta Rose, Plate 027; inside surface—a velvety intense Cardinal Red, Plate 822, edged with black and with base of petal Spiraea Red, Plate 025. Intermediate petal: outside surface—Rose Red, Plate 824; inside surface—a velvety Cardinal Red, Plate 822/1, with base of petal Spiraea Red, Plate 025. Inner petal: outside surface—Indian Lake, Plate 826, sometimes with a vein of Spiraea Red, Plate 025 extending from the base; inside surface—velvety Cardinal Red, Plate 822.

This description was made from a rose that was open for three days outdoors in the mouth of September at West Grove, Pennsylvania, U. S. A.:

*Color.*—Outer petal: outside surface—Indian Lake, Plate 826/1; inside surface—Cardinal Red, Plate 822, with base of petal Roseine Purple, Plate 629. Inner petal: outside surface—Rose Red, Plate 724/1; inside surface—Rose Red, Plate 724, with base of petal Rose Bengal, Plate 25/1.
*General color effect.*—Newly opened flower—Cardinal Red, Plate 822, sometimes shaded with darker tones in places. Three-days open—Rose Red, Plate 724.
*Behaviour.*—Drop off cleanly.

*Flower longevity.*—On bush in garden—5 days in September. Cut roses grown outdoors and kept at living room temperatures—5 days in September.

*Reproductive organs*

Stamens: Medium number; arranged irregularly about pistils.

Filaments: Medium number; most with anthers; medium length. Color—Carmine Rose, Plate 621, with upper quarter Mimosa Yellow, Plate 602/1.

Anthers: All open at once; medium size; occasionally an anther fused with a petaloid. Color—Primrose Yellow, Plate 601/1.

Pollen: Sparse. Color—yellow.

Pistils: Medium number.

Styles: Uneven; medium length; medium caliper; bunched.

Stigma: Color—whitish yellow.

Ovaries: Some protruding from receptacle.

Hips: None.

Sepals: Permanent; medium length; spear-shaped.

Seeds: None.

*Plant*

Foliage:

*Leaves.*—Compound of 3, 5 or 7 leaflets; normal abundance; medium size; leathery.

*Leaflets.*—Shape — roundly ovoid. Apex — acute. Base—obtuse. Margin—simply serrate.

*Color.*—Mature: upper surface — Parsley Green, Plate 00962; under surface—Sage Green, Plate 000861/1, washed with Erythrite Red, Plate 0027 on some leaves. Young: upper surface—Parsley Green, Plate 00962, overlaid with Maroon, Plate 1030; under surface—Sage Green, Plate 000861, overlaid with Erythrite Red, Plate 0027/1.

*Rachis (the supporting stem of the compound leaf).*—Medium caliper. Upper side—grooved; hairy. Under side—sparsely prickly.

*Stipules.*—Moderately long; medium width; with moderately long points turning out at an angle of more than 45°.

*Disease resistance.*—Average resistance to mildew and blackspot, as determined from comparison with other varieties grown under comparable conditions at West Grove, Pennsylvania, U. S. A.

Growth:

*Habit.*—Bushy; upright; much-branched.

*Growth.*—Vigorous.

*Canes.*—Medium caliper.

*Main stems.*—Color—Parsley Green, Plate 00962. Prickles—few; color—Fern Green, Plate 0862/1, overlaid with Oxblood Red, Plate 00823. Hairs—none.

*Branches.*—Color—Parsley Green, Plate 00962. Prickles—few; color—Fern Green, Plate 0862/1, overlaid with Oxblood Red, Plate 00823. Hairs—none.

*New shoots.*—Color—Garnet Brown, Plate 00918/1, overlying Parsley Green, Plate 00962. Prickles—few; color—Oxblood Red, Plate 00823. Hairs—none.

I claim:

A new and distinct variety of rose plant of the hybrid tea class, substantially as herein shown and described, characterized particularly as to novelty by its vigorous, bushy, much-branched and upright habit of growth, its abundant and attractive foliage which has good resistance to both mildew and blackspot, its flowering stems of a cutting length that is satisfactory for cut flowers when grown outdoors, its full, well-formed and exceptionally double flowers, and the intense, velvety Cardinal Red general color tonality of its flowers and the absence of fading of the flower color throughout the entire life of the flowers.

No references cited.